United States Patent
Ditzinger et al.

(10) Patent No.: US 8,697,122 B2
(45) Date of Patent: *Apr. 15, 2014

(54) FORMULATION FOR RETINOID-CONTAINING SOFT GELATIN CAPSULES

(75) Inventors: Günter Ditzinger, Freiburg (DE); Bernhard Gabriel, Oberuzwil (CH); Anne-Hortense Schmitt-Hoffmann, Basel (CH); Lutz Wevelsiep, Lörrach (DE)

(73) Assignee: Glaxo Group Limited, Greenford, Middlesex (GB)

(*) Notice: Subject to any disclaimer, the term of this patent is extended or adjusted under 35 U.S.C. 154(b) by 137 days.

This patent is subject to a terminal disclaimer.

(21) Appl. No.: 12/640,325

(22) Filed: Dec. 17, 2009

(65) Prior Publication Data

US 2010/0136108 A1   Jun. 3, 2010

Related U.S. Application Data

(63) Continuation of application No. 10/958,704, filed on Oct. 5, 2004, now abandoned.

(30) Foreign Application Priority Data

Nov. 3, 2003 (EP) .................................. 03405788

(51) Int. Cl.
*A61K 9/64* (2006.01)
*A01N 31/04* (2006.01)
*A61K 31/07* (2006.01)

(52) U.S. Cl.
USPC .......................................... 424/456; 514/725

(58) Field of Classification Search
USPC .......................................... 424/456; 514/725
See application file for complete search history.

(56) References Cited

U.S. PATENT DOCUMENTS

| 5,082,661 | A | 1/1992 | Melnik et al. |
| 5,428,071 | A | 6/1995 | Bollag et al. |
| 5,665,348 | A | 9/1997 | Okayama et al. |
| 5,855,826 | A | 1/1999 | Lee et al. |

(Continued)

FOREIGN PATENT DOCUMENTS

| EP | 0184942 | * | 6/1986 | ............. A61K 31/20 |
| EP | 0552624 | | 7/1993 | |

(Continued)

OTHER PUBLICATIONS

Pformulate, Pformulate a softgel!!!, Jun. 19, 2001, Pformulate, pp. 1-7 (note: 1st page is from archive.org to provide evidence of date).*
Gelatin, Oct. 12, 2001, Gelatin Food Science, pp. 1-9. http://www.gelatin.co.za/gltn1.html.*
European Search Report for EP03405788, co-related European application cited in Priority U.S. Appl. No. 10/958,704 (abandoned), Jul. 5, 2004.

*Primary Examiner* — Kevin S Orwig
*Assistant Examiner* — Trevor Love
(74) *Attorney, Agent, or Firm* — Dara L. Dinner; Theodore R. Furman

(57) ABSTRACT

A new pharmaceutical formulation for retinoid-containing soft gelatin capsules is disclosed. The new formulation comprises a soft gelatin capsule filled with a fill mass comprising a retinoid as an active ingredient, a natural vegetable oil, a partially hydrogenated natural vegetable oil and medium chain triglycerides. Optionally, the new formulation also comprises a natural wax. In a particularly preferred embodiment, the soft gelatin capsule comprises pig gelatin in the capsule shell in combination with the above fill mass.

2 Claims, 3 Drawing Sheets

Dosage 20 mg, Batch A, 12M, 30°C / 60% r.h.

(56) References Cited

U.S. PATENT DOCUMENTS 5,916,591 A 6/1999 Bierdel-Willkommen et al.
6,248,354 B1 6/2001 Firestone et al.
6,468,559 B1 * 10/2002 Chen et al. .................... 424/451
6,589,989 B1 7/2003 Bollag et al.

FOREIGN PATENT DOCUMENTS

| WO | 99/09969 | | 3/1999 | |
| WO | WO9924024 | * | 5/1999 | ............. A61K 31/00 |
| WO | 00/25772 | | 5/2000 | |
| WO | 01/95886 | | 12/2001 | |

* cited by examiner

Dosage 20 mg, Batch D, 9M, 40°C / 75% r.h.

Dosage 20 mg, Batch C, 9M, 40°C / 75% r.h.

Dosage 5 mg, Batch E, 9M, 40°C / 75% r.h.

Dosage 20 mg, Batch B, 1M, 40°C / 75% r.h.

FORMULATION FOR RETINOID-CONTAINING SOFT GELATIN CAPSULES

CROSS-REFERENCE TO RELATED APPLICATION

This application is a Continuation of U.S. Ser. No. 10/958,704 filed Oct. 5, 2004, now abandoned which claims priority from European Patent Application No. EP 03405788.5 filed on Nov. 3, 2003, the disclosure of which is incorporated herein in its entirety.

FIELD OF THE INVENTION

The present invention generally relates to a novel pharmaceutical formulation for retinoids in the form of a soft gelatin capsule.

BACKGROUND OF THE INVENTION

Retinoids are a class of compounds structurally related to vitamin A, comprising natural and synthetic compounds, which have been found to be clinically useful in dermatological, oncological and immunological diseases.

The activity of retinoids is thought to be mediated by the nuclear retinoid receptors as for example the known retinoid receptors RAR$\alpha$, $\beta$, and $\gamma$ or RXR$\alpha$, $\beta$, and $\gamma$. The activity of the retinoids may be an agonistic or antagonistic activity. Retinoids with receptor agonistic activity bind and activate receptors, whereas retinoids with receptor antagonistic activity bind receptors but do not activate them.

Specific examples for retinoids, which have been found to be clinically useful, are for example all-trans retinoic acid which is known to be effective in the treatment of acne, 13-cis retinoic acid which can be used in severe cases of acne (see Römpps Chemie Lexikon, 1987) or 9-cis retinoic acid, 9-cis retinal and 9-cis retinol as well as derivatives thereof, which are said to be clinically efficacious in the treatment of T-helper cell type 1 mediated immune diseases (WO 99/09969).

The retinoids or pharmaceutically acceptable derivatives thereof can generally be administered either topically or systemically.

Oral pharmaceutical preparations of retinoids are known for example from EP-A-0 552 624 A1, WO 00/25772 and WO 99/24024, describing tablets, sachets, aerosols for inhalation, soft and hard gelatin capsules.

A preferred oral dosage form is a soft gelatin capsule, as this material is easily dissolved in the digestive tract. An overview on soft gelatin capsules is for example given in Soft Gelatin Capsules Development, Tabibi, S. E. and Gupta, S. L., Editor: Liu, Rong, Water-Insoluble Drug Formation (2000), pp. 609-633, Interpharm Press, Buffalo Grove, Ill., USA. Moreover, in general, these preparations are favoured as they disguise the unpleasant taste and obnoxious odours that may be associated with the active pharmaceutical ingredient itself. They may also protect the active ingredient from oxygen and light induced degradation.

EP-A-0 552 624 A1, for example, discloses a soft gelatin capsule with a fill mass formulation consisting of 5-50 mg 9-cis retinoic acid, 1-3 parts of oil, and 1-5 parts of a wax mixture.

Furthermore, WO 99/24024 discloses a specific retinoid-containing soft gelatin capsule preparation containing 20 mg of active retinoid compound, with 0.028 mg DL-$\alpha$-tocopherol, 4.2 mg hydrogenated castor oil, 56.00 mg caprylic/capric/stearic triglycerides, and 199.772 mg medium chain triglycerides.

However, a crucial disadvantage of this formulation is that it exhibits very slow dissolution rates due to the formation of pellicles after long-term storage at temperatures above 5° C. This phenomenon increases with higher storage temperatures of the pharmaceutical preparation. Furthermore, in aqueous media, a non-dispersible fill mass and in some cases the formation of needles is observed.

SUMMARY OF THE INVENTION

Based on this state of the art, it is the object of the present invention to provide an improved retinoid-containing pharmaceutical soft gelatin capsule formulation having significantly improved dissolution properties and/or showing no tendency for pellicle formation and/or the formation of a non-dispersible fill mass or needles.

According to the present invention, there is provided a novel pharmaceutical formulation according to claim 1, which comprises a soft gelatin capsule filled with a fill mass comprising a retinoid as an active ingredient, a natural vegetable oil, a partially hydrogenated natural vegetable oil and medium chain triglycerides.

This novel formulation shows an excellent dissolution profile and neither pellicle formation nor a non-dispersible fill mass or needles as observed in the previously used formulation described on page 19, lines 14 ff. of WO 99/24024 mentioned above.

In a preferred embodiment of the present invention, the fill mass in addition comprises a natural wax, especially preferred yellow wax, to enhance the viscosity thereof and in order to prevent the suspended drug from sedimentation within the capsule.

Further preferred, the fill mass may also contain an antioxidant to avoid oxidation of the active compound on the one hand as well as of the natural oils on the other hand, and thus to increase the stability of the formulation.

The natural vegetable oil usable for the new formulation is preferably selected from soybean oil, corn oil, sunflower oil, rape seed oil, linseed oil, sesame oil, olive oil, coconut oil, peanut oil, safflower oil, castor oil and cottonseed oil or mixtures of two or more of these oils. Soybean oil is especially preferred as it is well tolerated and widely accepted.

The partially hydrogenated natural vegetable oils may also be selected from the oils mentioned above.

The medium chain triglycerides are normally selected from triglycerides of saturated fatty acids containing 8 to 10 carbon atoms, in particular from triglycerides of caprylic acid and/or capric acid.

The antioxidant is preferably selected from DL-a-tocopherol, butylhydroxy toluene (BHT) and butylhydroxy anisole (BHA).

The shell of the soft gelatin capsule normally comprises gelatin, one or more plasticizers and water.

The plasticizers are preferably selected from the group consisting of glycerol, sorbitol, propylene glycol, and mixtures of these components. More preferably, the plasticizers comprise a mixture of glycerol and sorbitol. The plasticizers are important to provide elasticity to the soft gelatin capsules.

The gelatin used in the soft capsule shell preferably is pig gelatin which is in particular derived from pig skin.

BRIEF DESCRIPTION OF THE DRAWINGS

FIG. 2, the middle graph in this figure is a graph of dissolution curve a 20 milligram soft gelatin capsule filled with the ingredients of Batch C in accordance with this invention.

FIG. 2, the bottom graph in this figure is a graph of the dissolution curve of a 5 milligram soft gelatin capsule filled with the ingredients of Batch E in accordance with this invention.

DETAILED DESCRIPTION OF THE INVENTION

Figure 1:
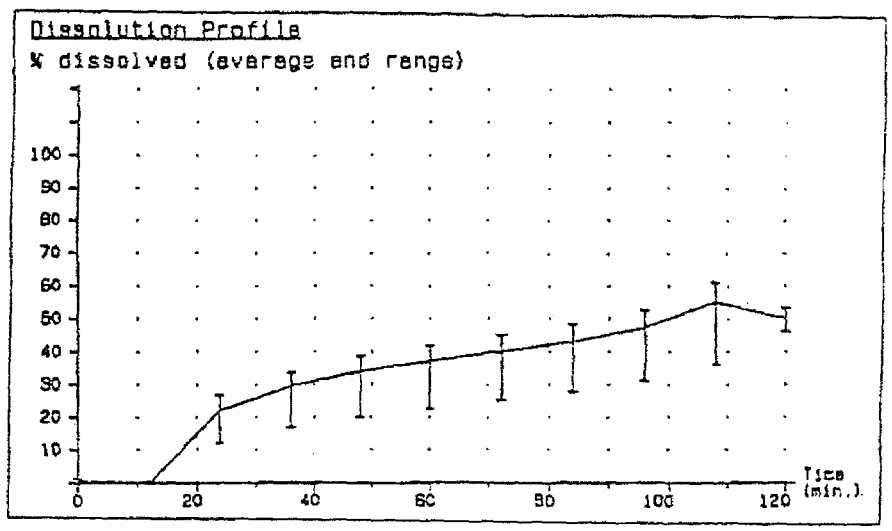
FIG. 1. is a graph of a dissolution curve of a soft bovine gelatin capsule containing the fill of Batch A prepared in accordance with the prior art reference, WO 99/24024.

According to the present invention it was found that there is an unexpected synergistic effect with regard to the dissolution characteristics of the pharmaceutical formulation when pig gelatin in the capsule shell is used in combination with the new fill mass formulation. This effect was not observed when a combination of bovine gelatin with the new fill mass or pig gelatin with the previously used fill mass of WO 99/24024 was used. However, also the new fill mass combined with bovine gelatin was superior compared to the combination of bovine gelatin with the old fill mass.

In addition, the use of pig gelatin in this formulation also has the advantage that it avoids regulatory issues associated with the use of bovine gelatin, namely the occurrence of Bovine Transmissible Spongiform Encephalopathies.

The retinoid contained as active ingredient in the pharmaceutical formulation can be selected from the group consisting of retinol, retinal, retinoic acid and derivatives thereof. Specific examples are all-trans retinol, all-trans retinoic acid, 13-cis retinoic acid and 9-cis retinoic acid. The retinoids may also be present in the form of pharmaceutically acceptable derivatives like salts, esters or prodrugs.

The fill mass contained in the soft gelatin capsule preferably comprises about 50 to 80 percent by weight, in particular about 60 to 70 percent by weight, especially preferred about 62 to 64 percent by weight, of the natural vegetable oil, about 15 to 35 percent by weight, in particular about 20 to 30 percent by weight, especially preferred about 24 to 25 percent by weight, of the hydrogenated natural vegetable oil, and about 3 to 20 percent by weight, in particular about 6 to 12 percent by weight, especially preferred about 8 to 9 percent by weight, of the medium chain triglycerides.

In cases where the fill mass also comprises a natural wax, the fill mass preferably comprises about 1 to 10 percent by weight, in particular about 3 to 6 percent by weight, especially preferred about 4 percent by weight, of the natural wax, most preferred yellow wax.

Due to the above mentioned synergistic effect between fill mass and capsule shell regarding the in-vitro dissolution characteristics, a particularly preferred pharmaceutical formulation according to the present invention is a formulation comprising a soft gelatin capsule shell containing pig gelatin, glycerol, sorbitol, and water, and a fill mass containing a retinoid, in particular 9-cis retinoic acid, as the active ingredient, soybean oil, hydrogenated soybean oil, medium chain triglycerides, yellow wax, and DL-a-tocopherol.

Other pharmaceutically acceptable additives like colorants, flavoring agents, stabilizers, emulsifying agents and so on may also be added, if desired.

The invention will now be described in greater detail by reference to the following non-limiting examples.

EXAMPLES

Soft gelatin capsules according to the prior art and according to the present invention were produced in line with a standard manufacturing process schematically described below in compliance to cGMP requirements. Each manufacturing step (as appropriate) was performed under yellow light and inert atmosphere (nitrogen).

For manufacturing the fill mass, the triglyceride and oil components of the fill mass are weighed into a suitable stainless steel vessel, heated to a maximum of 70° C., and cooled to room temperature at constant stirring. If applicable, an antioxidant, e.g. DL-a-tocopherol, is added to the resulting mixture which is then stirred at room temperature for about 30 minutes.

Subsequently, a retinoid, e.g. 9-cis retinoic acid, is added to the above blend and stirred until a homogenous suspension is obtained. The suspension is stored in a stainless steel vessel under inert gas at reduced pressure, tightly sealed and protected from light until encapsulation.

The encapsulation of the homogenous suspension into the gelatin shell is then carried out on a rotary-dye machine as it is well known in the prior art (see for example Bauer, K. H. et al., Lehrbuch der Pharmazeutischen Technologie, $6^{th}$ ed., pp. 343-348, Stuttgart, 1999)

Comparative Example 1

Batch A

A soft gelatin capsule formulation according to the prior art as described in WO 99/24024 was prepared as outlined above, using the following components for the fill mass and the capsule shell:

Old Fill Mass:

| Compound | mg/capsule |
| --- | --- |
| Alitretinoin (9-cis retinoic acid) | 20.00 |
| DL-a-Tocopherol | 0.028 |
| Hydrogenated castor oil | 4.200 |
| Medium chain triglycerides (Miglyol ® 812, MCT) | 199.772 |
| Caprylic/capric/stearic triglyceride (Softisan ® 378, synthetic triglycerides) | 56.00 |

Miglyol ® 812 and Softisan ® 378 were obtained from Sasol, Witten, Germany. DL-a-Tocopherol was from Roche Vitamins, Sisseln, Switzerland. Hydrogenated castor oil and alitretinoin were provided by Hoffmann La-Roche, Basel, Switzerland.

Capsule Shell:

| Compound | mg/capsule |
| --- | --- |
| Bovine Gelatin | 80.85 |
| Glycerol (98-101%) | 24.53 |
| Sorbitol, liquid, non-crystallizing | 15.09* |
| Water, purified | 13.33** |
| Iron oxide, red (E 172) | 0.595 |
| Iron oxide, yellow (E 172) | 0.595 |

(*calculated as dry matter, **calculated amount in shell after drying)

In the Examples and Comparative Examples, all gelatins were obtained from DGF Stoess, Eberbach, Germany, glycerol was from Uniqema, Emmerich, Germany, Sorbitol, liquid, non-crystallizing, was from Merck, Darmstadt, Germany, iron oxide red and yellow were obtained from BASF, Ludwigshafen, Germany, yellow wax was from Kahl, Trittau, Germany, soybean oil as well as partially hydrogenated soybean oil were from Florin, Muttenz, CH.

Dissolution tests were carried out with the prior art formulation of Comparative Example 1. It was found that the mixture Miglyol® 812/Softisan® 378/hydrogenated castor oil exhibited problems in dissolution testing due to the formation of pellicles after storage at elevated temperatures. Already after 1 week at 40° C., the fill mass was covered in the dissolution test by a visible film. In addition, lumps of a non-dispersible fill mass were observed.

A dissolution curve of a soft gelatin capsule according to Comparative Example 1 (Batch A) is shown in FIG. 1. Even at optimised dissolution test conditions, the profile flattens out at higher temperatures, most likely due to the above mentioned effects. The dissolution rates for samples stored at 40° C. already after 1 month rarely exceeded 200 (data not shown).

Example 2

Batch D

A soft gelatin capsule formulation according to the present invention was prepared by the above described process, using the following components:

New fill mass according to the present invention:

| Compound | mg/capsule |
| --- | --- |
| Alitretinoin (9-cis retinoic acid) | 20 |
| Soybean oil | 162.00 |
| Partially hydrogenated soybean oil | 65.00 |
| Medium chain triglycerides (Migyol ® 812) | 23.00 |
| Yellow wax | 10.00 |
| DL-α-tocopherol | 0.028 |

Capsule Shell:

| Compound | mg/capsule |
| --- | --- |
| Pig gelatin | 82.0 |
| Sorbitol, liquid, non-crystallizing | 22.3* |
| Glycerol (98-101%) | 16.5 |
| Water, purified | 13.6** |
| Iron oxide, red (E 172) | 0.60 |
| Iron oxide, yellow (E 172) | 0.60 |

(*calculated as dry matter, **calculated amount in shell after drying)

Example 3

Batch C

A further soft gelatin capsule formulation according to the present invention was prepared as in Example 2. However, while the fill mass was identical to the fill mass of Example 2, the capsule shell contained bovine gelatin instead of pig gelatin, and its composition was as follows:

Capsule Shell:

| Compound | mg/capsule |
| --- | --- |
| Bovine gelatin | 82.0 |
| Sorbitol, liquid, non-crystallizing | 15.3* |
| Glycerol (98-101%) | 26.4 |
| Water, purified | 14.6** |
| Iron oxide, red (E 172) | 0.60 |
| Iron oxide, yellow (E 172) | 0.60 |

(*calculated as dry matter, **calculated amount in shell after drying)

Example 4

Batch E

A further soft gelatin capsule formulation according to the present invention was prepared using the fill mass of Example 2, except that only 5 mg alitretinoin were present and 15 mg additional soybean oil were added instead, and the following composition for the capsule shell:

Capsule Shell:

| Compound | mg/capsule |
| --- | --- |
| Pig gelatin | 82.0 |
| Sorbitol, liquid, non-crystallizing | 16.5* |
| Glycerol (98-101%) | 22.3 |
| Water, purified | 13.6** |

(*calculated as dry matter, **calculated amount in shell after drying)

The formulations according to Examples 2 to 4 were found to be sufficiently stable for at least 12 months at temperatures up to 30° C.

Comparative Example 5

Batch B

A further soft gelatin capsule formulation based on the old fill mass formulation of Comparative Example 1 was prepared using the capsule shell composition of Example 2.

Figure 2:
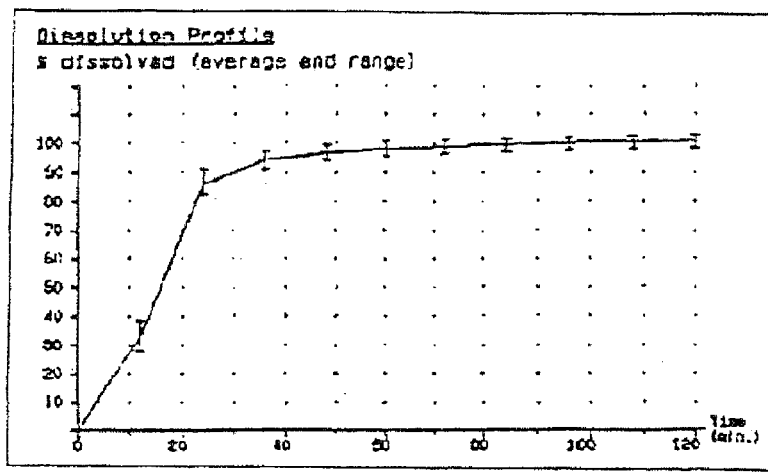
FIG. 2, the top graph in this figure is a graph of the dissolution curve of a soft gelatin capsule filled with the ingredients of Batch B in accordance with this invention.
Figure 2:
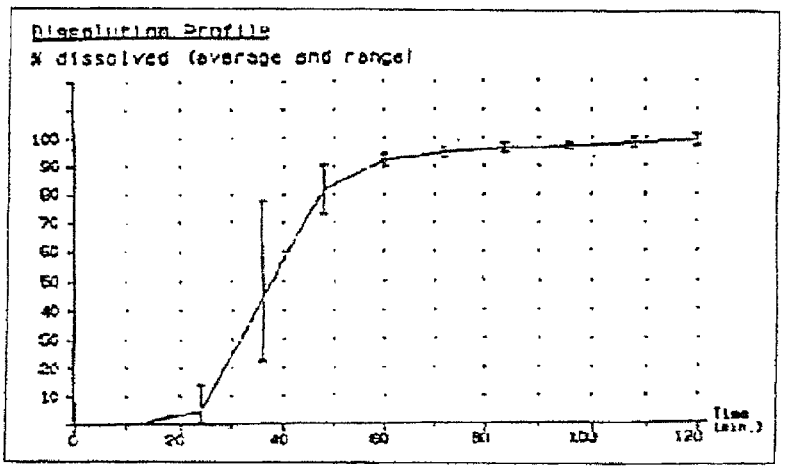
Figure 2:
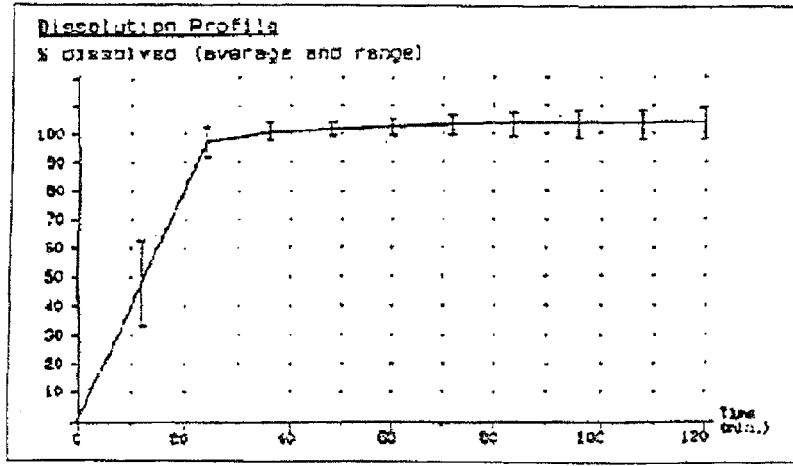
Figure 3:
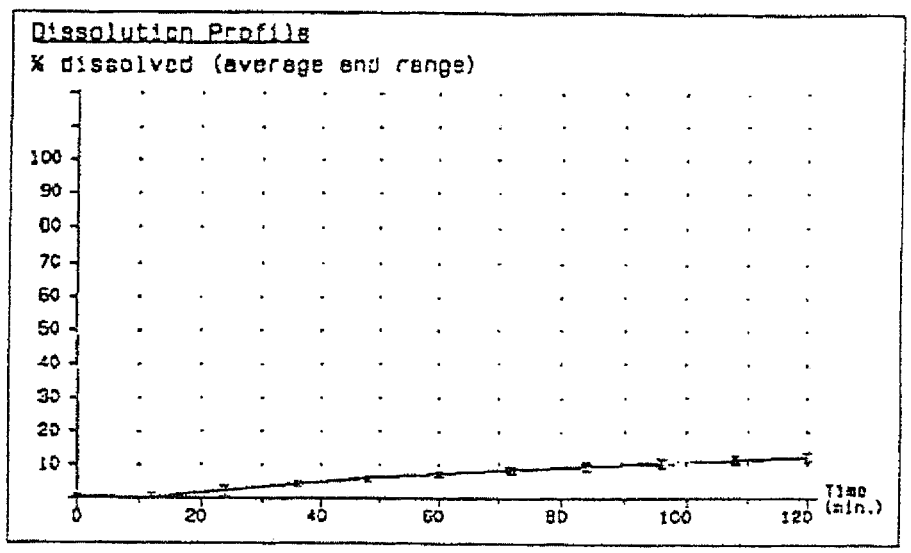
FIG. 3 is a graph of a dissolution curve of a soft gelatin capsule formulation filled with the filled mask of the prior art as described in WO 99/24024 in a pig gelatin capsule shell.

Dissolution tests with the formulations of Examples 2 to 4 (Batches D, C and E) and Comparative Example 5 (Batch B) were carried out for samples stored at 40° C./75% relative humidity (r.h.) to speed up the detection of possible differences in the dissolution profiles of the variants. The dissolution curves of the formulations of Examples 2 to 4 are shown in FIG. 2, and the dissolution curve of Comparative Example 5 is shown in FIG. 3.

Whereas the dissolution curve of Comparative Example 5 using the old fill mass exhibited the same poor dissolution behaviour as Comparative Example 1, the dissolution curves of Examples 2 to 4 showed significantly improved dissolution profiles. The new formulations according to the present invention released the drug almost completely in a short time in the same dissolution test set-up. These results could be reproduced even after 12 months storage under the same accelerated storage conditions.

Finally, the chemical stability of the active ingredient suspended in the fill mass formulation of Comparative Example 1 as well as the one of Example 2 were tested during a storage period of 6 months, and the amount of degradation products (including degradation products like 13-cis retinoic acid and all-trans retinoic acid as well as unspecified degradation products) was determined. The comparative results of the stability test are shown in the following table.

| | Storage Conditions 6 months, 40° C./75% r.h. | |
|---|---|---|
| | Fill mass from Comparative Example 1 | Fill mass from Example 2 |
| Total amount of degradation products | 1.49% | 0.98% |

As may be seen from this table, the total amount of degradation products could be reduced from 1.49% for the formulation according to the prior art to 0.98% for the formulation according to the present invention.

In addition, the same stability test as described above was also conducted with fill mass formulations of Comparative Example 1 and Example 2 containing only 5 mg of the active ingredient instead of 20 mg, together with 15 mg additional soybean oil (Comparative Example 1) or 15 mg additional Miglyol® 812 (Example 2). In this case, the total amount of degradation products could even be reduced from 2.93% to 1.64% (corresponding to a reduction of about 50%).

This improved chemical stability is a further benefit of the new formulation according to the present invention.

What is claimed is:

1. A soft gelatin capsule comprising a shell filled with a fill mass comprising 20.00 mg of 9-cis-retinoic acid or pharmaceutically acceptable salts thereof as an active ingredient, 162.00 mg of soybean oil, 65.00 mg of partially hydrogenated soy bean oil, 23.00 mg of medium chain triglyceride selected from triglycerides of saturated fatty acids containing 8 to 10 carbon atoms, and 10.00 mg of natural wax wherein the soft gelatin shell is selected from the group consisting of
   a) a capsule shell comprising 82 mg of pig gelatin, 22.3 mg of sorbitol, 16.5 mg of glycerol and 13.6 mg of water; and
   b) a capsule shell comprising 82.0 mg of bovine gelatin, 15.3 mg of sorbitol, 26.4 mg of glycerol and 14.6 mg of water.

2. The soft gelatin capsule of claim 1 wherein said natural wax is yellow wax; said triglyceride is caprylic acid, capric acid, or a mixture of caprylic acid and capric acid; and additionally having an antioxidant selected from DL-α-tocopherol, butylhydroxy toluene (BHT) and butylhydroxy anisole (BHA).

* * * * *